US012667378B2

(12) United States Patent
O'Brien et al.

(10) Patent No.: US 12,667,378 B2
(45) Date of Patent: Jun. 30, 2026

(54) THROMBECTOMY DEVICE

(71) Applicant: VETEX MEDICAL LTD, Galway (IE)

(72) Inventors: Con O'Brien, Galway (IE); Shane Molloy, Galway (IE); John Egan, Galway (IE); Mark Bruzzi, Galway (IE)

(73) Assignee: Vetex Medical Limited, Galway (IE)

( * ) Notice: Subject to any disclaimer, the term of this patent is extended or adjusted under 35 U.S.C. 154(b) by 118 days.

(21) Appl. No.: 18/287,430

(22) PCT Filed: Apr. 22, 2022

(86) PCT No.: PCT/EP2022/060671
§ 371 (c)(1),
(2) Date: Oct. 18, 2023

(87) PCT Pub. No.: WO2022/223772
PCT Pub. Date: Oct. 27, 2022

(65) Prior Publication Data
US 2024/0215997 A1 Jul. 4, 2024

(30) Foreign Application Priority Data
Apr. 22, 2021 (EP) .................................... 21169975

(51) Int. Cl.
*A61B 17/22* (2006.01)
*A61B 17/221* (2006.01)

(52) U.S. Cl.
CPC .... *A61B 17/221* (2013.01); *A61B 2017/2212* (2013.01); *A61B 2017/2215* (2013.01)

(58) Field of Classification Search
CPC .......... A61B 17/221; A61B 17/320725; A61B 17/32; A61B 17/320016; A61B 17/32002;
(Continued)

(56) References Cited

U.S. PATENT DOCUMENTS

2001/0031981 A1* 10/2001 Evans ............ A61B 17/320725
606/159
2002/0010487 A1 1/2002 Evans et al.
(Continued)

FOREIGN PATENT DOCUMENTS

EP 0117519 9/1984
EP 0117519 A1 9/1984
(Continued)

OTHER PUBLICATIONS

"European Application Serial No. 21169975.6, Communication Pursuant to Article 94(3) EPC mailed Dec. 7, 2023", 3 pgs.
(Continued)

*Primary Examiner* — Kathleen S Holwerda
(74) *Attorney, Agent, or Firm* — Schwegman Lundberg & Woessner, P.A.

(57) ABSTRACT

A thrombectomy device (1) for removing matter from a body lumen comprising a handle (3), a catheter member (2) extending from the handle (3) having a distal control arm (5) and a proximal control arm (6), a radially expansible member (4) on the distal control arm radially expansible between a contracted position and an expanded, thrombus-capture, position in response to axial movement of the distal control arm (5); and a thrombus extraction mechanism (14) extending through the distal control arm (5) wherein the extraction mechanism (14) and the distal control arm (5) are coupled to enjoy a synchronised axial movement so that the extraction mechanism (14) is positionally axially fixed with respect to the distal control arm (5).

13 Claims, 9 Drawing Sheets

(58) Field of Classification Search
CPC ............ A61B 17/3205; A61B 17/3207; A61B
17/320708; A61B 17/320783; A61B
2017/320024; A61B 2017/320028; A61B
2017/320032; A61B 2017/32004; A61B
2017/320775; A61B 2017/2212; A61B
2017/2215; A61B 2017/2217
See application file for complete search history.

(56) References Cited

U.S. PATENT DOCUMENTS

| | | | |
|---|---|---|---|
| 2004/0219028 A1 | 11/2004 | Demarais et al. | |
| 2010/0076476 A1* | 3/2010 | To ..................... | A61B 17/1671 |
| | | | 606/170 |
| 2013/0225943 A1* | 8/2013 | Holsing .................. | A61B 6/12 |
| | | | 600/409 |
| 2016/0038174 A1* | 2/2016 | Bruzzi ............. | A61B 17/32056 |
| | | | 606/159 |
| 2017/0333076 A1 | 11/2017 | Bruzzi et al. | |
| 2020/0187976 A1* | 6/2020 | Cartier ................. | A61B 17/221 |

FOREIGN PATENT DOCUMENTS

| | | | |
|---|---|---|---|
| EP | | 3305221 A1 | 4/2018 |
| EP | | 4079239 B1 | 7/2025 |
| WO | WO-2022223772 A1 | | 10/2022 |

OTHER PUBLICATIONS

"European Application Serial No. 21169975.6, Response filed Mar. 27, 2024 to Communication Pursuant to Article 94(3) EPC mailed Dec. 7, 2023", 10 pgs.

"International Application Serial No. PCT EP2022 060671, Response filed Feb. 22, 2003 to Written Opinion mailed Jul. 28, 2022", (Feb. 22, 23), 12 pgs.

"European Application Serial No. 21169975.6, Extended European Search Report mailed Oct. 7, 2021", 6 pgs.

"International Application Serial No. PCT/EP2022/060671, International Search Report mailed Jul. 28, 2022", 4 pgs.

"International Application Serial No. PCT/EP2022/060671, Written Opinion mailed Jul. 28, 2022", 6 pgs.

* cited by examiner

THROMBECTOMY DEVICE

PRIORITY APPLICATION

This application is a U.S. National Stage Filing under 35 U.S.C. 371 from International Patent Application Serial No. PCT/EP2022/060671, filed Apr. 22, 2022, which application is a continuation of and claims priority to European Patent Application No. 21169975.6, filed Apr. 22, 2021, the contents of which are incorporated herein by reference in entireties.

PRIORITY APPLICATION

This application is a continuation of and claims priority to European Patent Application No. 21169975.6, filed Apr. 22, 2021, the content of which is incorporated herein by reference in its entirety.

TECHNICAL FIELD

The invention provides a device for removing matter such as thrombus from a body lumen such as a blood vessel. In particular, the invention provides a thrombectomy device for removing thrombus from blood vessels.

BACKGROUND OF THE INVENTION

Thrombectomy devices made up of an elongate catheter attached to a handle in which the elongate catheter has a distal part and a proximal part with a thrombus capture body in the form of a radially expansible member such as a cage disposed on the distal part of the catheter which is radially expansible between a contracted orientation and an expanded, thrombus-capture, orientation are widely used in human and animal medicine. Typically, the radially expansible member has an open end for receipt of thrombus and the device is provided with control arms to move the thrombus capture body between the contracted and expanded orientations.

Some thrombectomy devices are also provided with extraction mechanisms located in or adjacent to the radially expansible member that serve to extract captured thrombus from the thrombectomy device.

However, known thrombectomy devices can suffer from a number of disadvantages. As the radially expansible member must be moved between the contracted and expanded orientations, the relative positions of elements of the thrombectomy device can shift, e.g. in an axial direction along the catheter, into positions that are sub-optimal in use. For example, undesired movement of the extraction mechanism or the opening into the extraction mechanism can severely compromise extraction performance. More generally, uncontrolled positional shifts of elements within the thrombectomy device can reduce the efficacy of the devices.

In addition, regardless of the problems associated with uncontrolled relative movement of elements of the device outlined above, the radially expansible members and extraction mechanisms employed in the thrombectomy devices of the prior art can sometimes fail to capture and extract thrombus as efficiently as possible.

An object of the invention is to overcome at least some of the problems of the prior art.

SUMMARY OF THE INVENTION

According to the invention there is provided a thrombectomy device for removing matter from a body lumen comprising:

a handle a catheter member extending from the handle having a distal control arm and a proximal control arm;

a radially expansible member on the distal control arm radially expansible between a contracted position and an expanded, thrombus-capture, position in response to axial movement of the distal control arm; and a thrombus extraction mechanism extending through the distal control arm wherein the extraction mechanism and the distal control arm are coupled to enjoy a synchronised axial movement so that the extraction mechanism is positionally axially fixed with respect to the distal control arm.

In any embodiment, the extraction mechanism and the distal control arm are configured to be coupled at the handle to effect the synchronised axial movement.

Preferably, the extraction mechanism comprises a helical coil.

In a preferred embodiment, the thrombectomy device comprises at least one extraction window on the distal control arm wherein the extraction window is positionally axially fixed with respect to the helical coil and, optionally, the extraction window has a longitudinal and circumferential axis along the distal control arm.

Preferably, in any embodiment, the helical coil comprises a shorter pitch at or adjacent the extraction window and a longer pitch towards the handle.

Alternatively or in addition, the helical coil comprises a distal small diameter coil portion at or adjacent the extraction window and a proximal large diameter coil portion contiguous with the small diameter coil portion towards the handle.

Optionally, in any embodiment, the helical coil has a variable thickness or cross-sectional area.

Preferably, the extraction mechanism further comprises a coil rotation mechanism in or adjacent to the handle. In any embodiment, the coil rotation mechanism comprises a drive train slidably connected to the helical coil to facilitate axial translation of the helical coil.

In any embodiment, the helical coil and the distal control arm are coupled at a biasing mechanism in the handle. Preferably, the biasing mechanism biases the extraction mechanism proximally and/or distally relative to the proximal arm.

Optionally, in any embodiment, the thrombectomy device further comprises a manually operable over-ride mechanism to over-ride the biasing mechanism.

In one embodiment, the thrombectomy device further comprises a guide wire lumen through the catheter member. Preferably, the helical coil is positioned over the guide wire lumen and the guidewire lumen is not rotationally coupled to the helical coil.

Optionally, in any embodiment, the thrombectomy device further comprises an extraction port in fluid communication with the extraction mechanism for extracting thrombus from the extraction mechanism.

In any embodiment, the helical coil is connected to the distal control arm at one end thereof.

In any embodiment, the guidewire lumen is axially moveable relative to the distal control arm.

Optionally, in any embodiment, the coil rotation mechanism is axially fixed to the distal control arm. Alternatively, the coil rotation mechanism is fixedly attached to the handle.

The invention also extends to a thrombectomy device further comprising an operative connection between the helical coil and the coil rotation mechanism.

In any embodiment, device elements can be configured to be rotatable if desired. In one embodiment, the device is configured to facilitate rotation of the expansible member and the distal/proximal control arms to aid in separating thrombus from vessel walls.

Additional guides 34 can facilitate the rotation movement thereby providing a mechanism for components to slide and rotate as required.

In any embodiment, the radially expansible member is provided with one or more radially expansible member blockers to prevent radially expansible member inversion in use. Suitably, the blockers are a pair of oppositely disposed spaced blockers.

The invention also extends to a thrombectomy device for removing matter from a body lumen comprising:
   a handle
   a catheter member extending from the handle having a distal control arm and a proximal control arm;
   a radially expansible member on the distal control arm radially expansible between a contracted position and an expanded, thrombus-capture, position in response to axial movement of the distal control arm;
   a thrombus extraction mechanism extending through the distal control arm and an extraction port in fluid communication with the extraction mechanism for extracting thrombus from the extraction mechanism.

Preferably, the extraction mechanism and the distal control arm are coupled to enjoy a synchronised axial movement so that the extraction mechanism is positionally axially fixed with respect to the distal control arm.

In another embodiment, the invention extends to a thrombectomy device for removing matter from a body lumen comprising:
   a handle
   a catheter member extending from the handle having a distal control arm and a proximal control arm;
   a radially expansible member on the distal control arm radially expansible between a contracted position and an expanded, thrombus-capture, position in response to axial movement of the distal control arm;
   a thrombus extraction mechanism extending through the distal control arm and
   an outer sheath on the proximal control arm to prevent the device from causing vessel trauma when navigating to a treatment zone.

Optionally, the outer sheath is axially slidably moveable to expose and cover the expansible member in use as required.

In one embodiment, the device is provided with guides to facilitate the axial movement of the sheath.

Preferably, the extraction mechanism and the distal control arm are coupled to enjoy a synchronised axial movement so that the extraction mechanism is positionally axially fixed with respect to the distal control arm.

The invention also extends to The invention also extends to a thrombectomy device for removing matter from a body lumen comprising:
   a handle
   a catheter member extending from the handle having a distal control arm and a proximal control arm;
   a radially expansible member on the distal control arm radially expansible between a contracted position and an expanded, thrombus-capture, position in response to axial movement of the distal control arm; and
   a thrombus extraction mechanism comprising a helical coil extending through the distal control arm wherein the helical coil comprises a small diameter coil portion and a large diameter coil portion contiguous with the small diameter coil portion.

In one embodiment, the extraction mechanism comprises an extraction lumen made up of a relatively smaller diameter extractor lumen portion and a relatively larger diameter lumen portion.

Optionally, the small diameter coil portion may be the same as the large diameter coil portion within the small and large diameter lumen portions.

In any embodiment of the invention described herein, the shorter pitch can transition to the longer pitch at a pitch transition zone. Preferably the pitch transition zone starts within a distance defined by approximately 10 times the pitch distal to the proximal end of an extraction window 16 to minimise the distance material travels at the short pitch and reduce the potential for the extraction mechanism to block in use. In one embodiment, the length of the transition zone is preferably less than a distance defined by 10 times the distal pitch.

In any embodiment of the invention, the helical coil comprises an elongate wire having a variable thickness or cross-sectional area.

In any embodiment the helical coil may comprise coiled wire(s) or cut tube profiles with different cross sectional profiles, including round, ovoid, square, rectangular, triangular or other profiles suitable for cutting and extraction when rotated.

The invention also extends to a thrombectomy device for removing matter from a body lumen comprising:
   a handle
   a catheter member extending from the handle having a distal control arm and a proximal control arm;
   a radially expansible member on the distal control arm radially expansible between a contracted position and an expanded, thrombus-capture, position in response to axial movement of the distal control arm;
   a thrombus extraction mechanism comprising an extraction window extending through the distal control arm wherein the extraction window is positioned within and/or proximal and/or distal to the radially expansible member.

Preferably, the extraction window is located or positioned within the radially expansible member. More preferably, the extraction window is located towards a distal end of the radially expansible member. Alternatively or in addition, the extraction window is located proximal to and outside the radially expansible member.

In one embodiment, the extraction window has both a longitudinal and circumferential axis along the distal control arm.

Preferably, the extraction mechanism and the distal control arm are coupled to enjoy a synchronised axial movement so that the extraction mechanism is positionally axially fixed with respect to the distal control arm.

In another embodiment, the invention extends to a thrombectomy device for removing matter from a body lumen comprising:
   a handle
   a catheter member extending from the handle having a distal control arm and a proximal control arm;
   a radially expansible member on the distal control arm radially expansible between a contracted position and an expanded, thrombus-capture, position in response to axial movement of the distal control arm; and
   a thrombus extraction mechanism extending through the distal control arm wherein the radially expansible member comprises a braided cage having distinguishable distal, central flexible and proximal zones.

Optionally, the radially expansible member is formed from braided or twisted material such as wires. Alternatively or in addition, the radially expansible member is formed from a cut or formed profile to form the distal, central flexible and proximal zones.

Preferably, the extraction mechanism and the distal control arm are coupled to enjoy a synchronised axial movement so that the extraction mechanism is positionally axially fixed with respect to the distal control arm.

By coupling and synchronising axial movement of the helical coil and the distal control arm it is ensured that the relative positions of the extraction mechanism and the distal control arm are maintained in use. More particularly, the relative positions of the extraction window in the distal control arm and the extraction mechanism such as the helical coil are maintained to ensure optimal extraction. Importantly, the relative positioning of the transition zone in helical coils having a variable pitch to the extraction zone is maintained to ensure optimal extraction. In short, in use, as the extraction mechanism is disposed within the distal control arm and can be moved in concert with the radially expansible member as the radially expansible member is moved between the expanded and contracted positions, the position of the extraction mechanism, and in particular the position of the shorter pitch in an extraction mechanism made up of the helical coil having a variable pitch, relative to the extraction window is maintained. Other benefits of the thrombectomy devices of the invention are outlined further below.

BRIEF DESCRIPTION OF THE DRAWINGS

The invention will now be described, by way of example only, with reference to the accompanying drawings in which.

6

Figure 8:
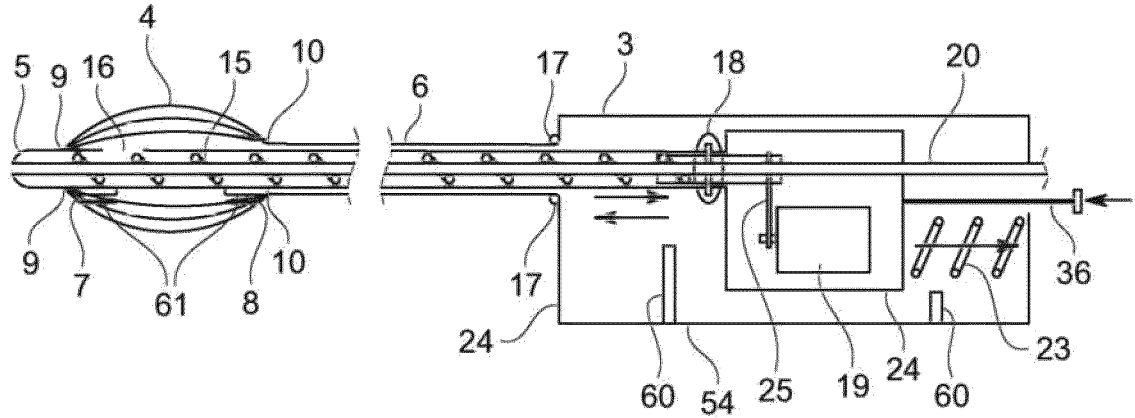
Figure 9:
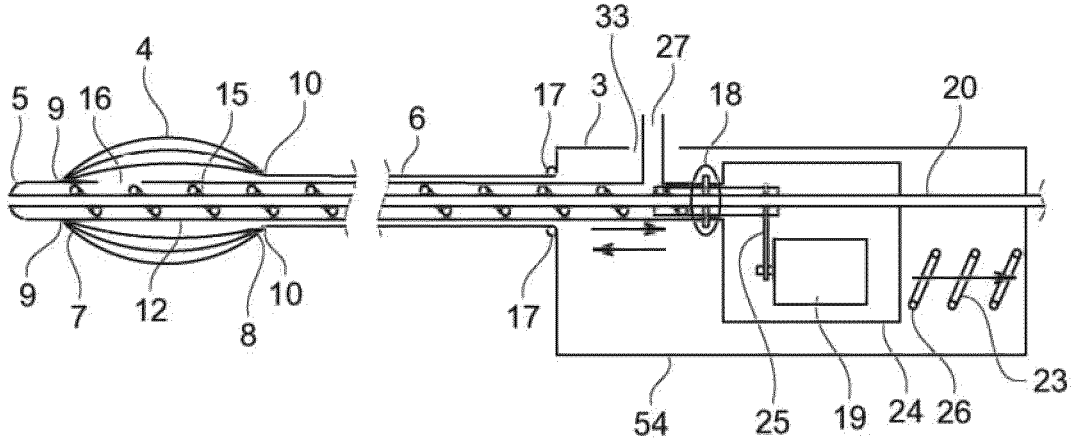
Figure 10:
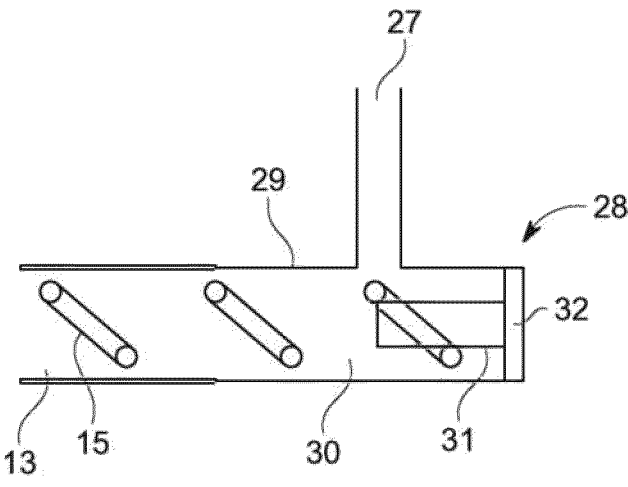
Figure 11:
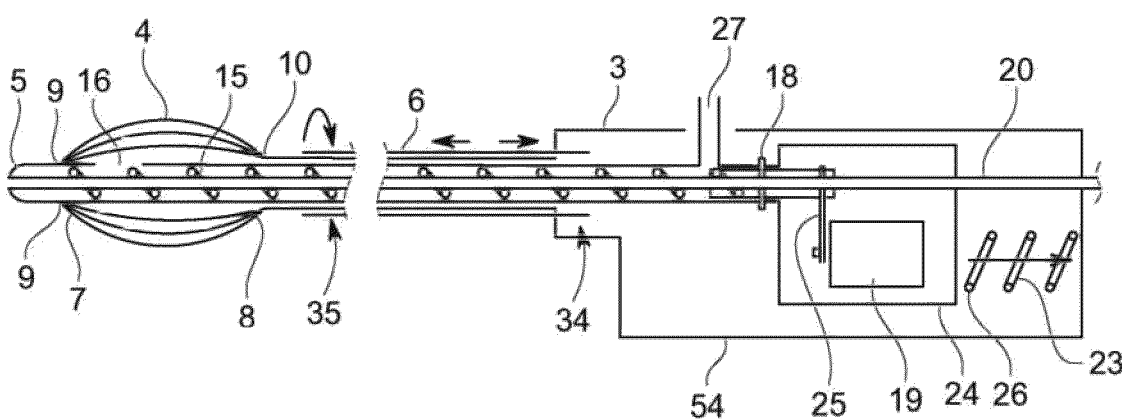
Figure 12:
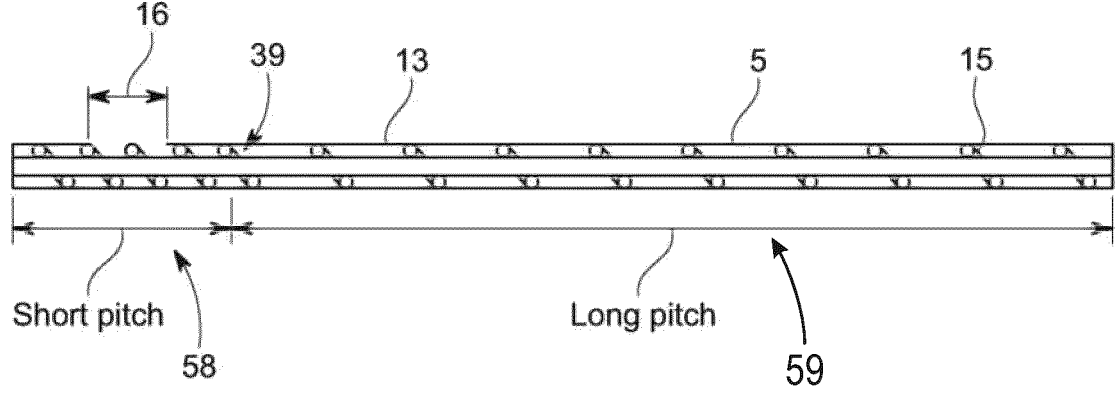
Figure 13:
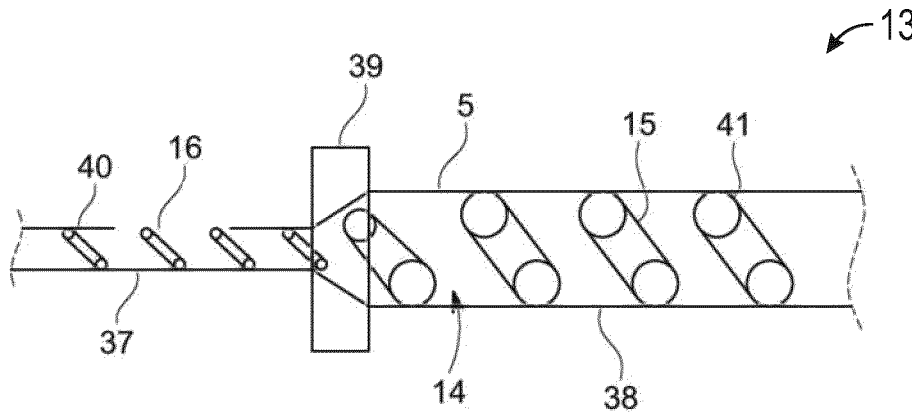
Figure 14:
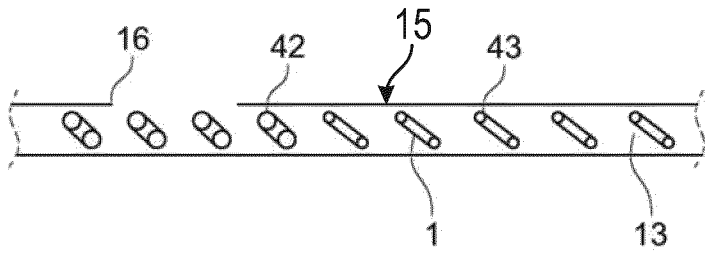
Figure 15:
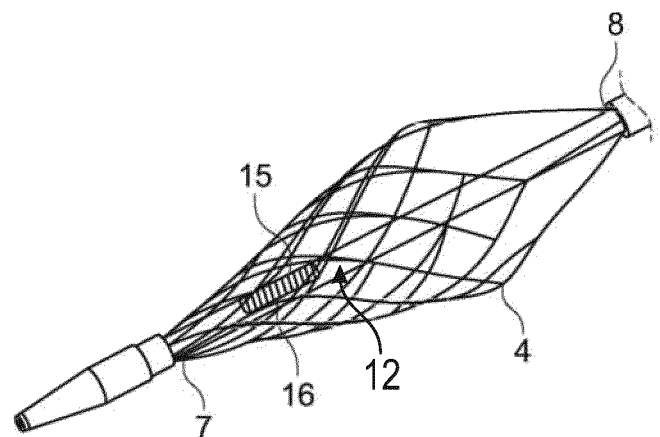
Figure 16:
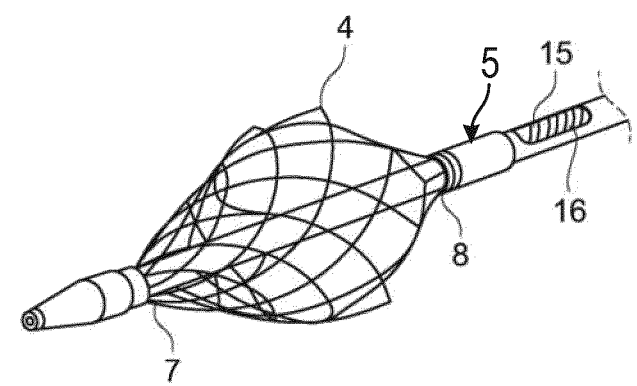
Figure 17:
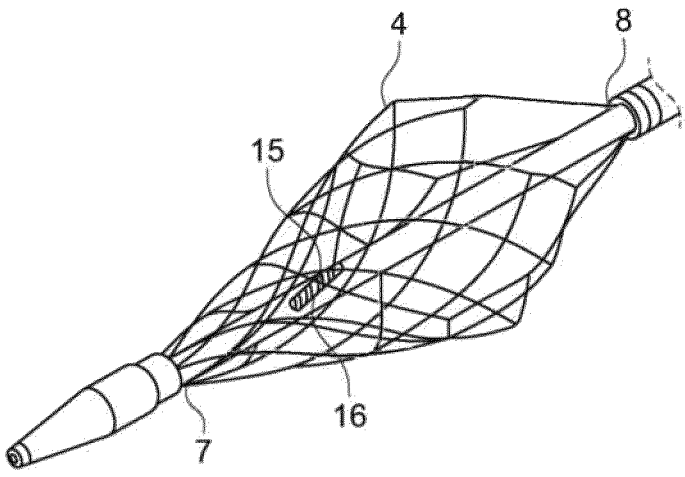
Figure 18:
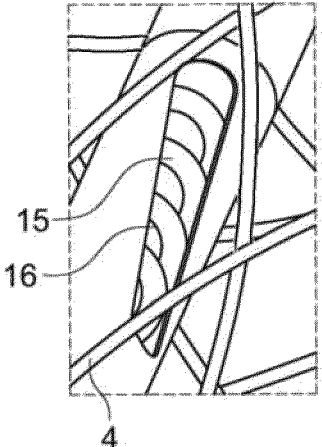
Figure 19:
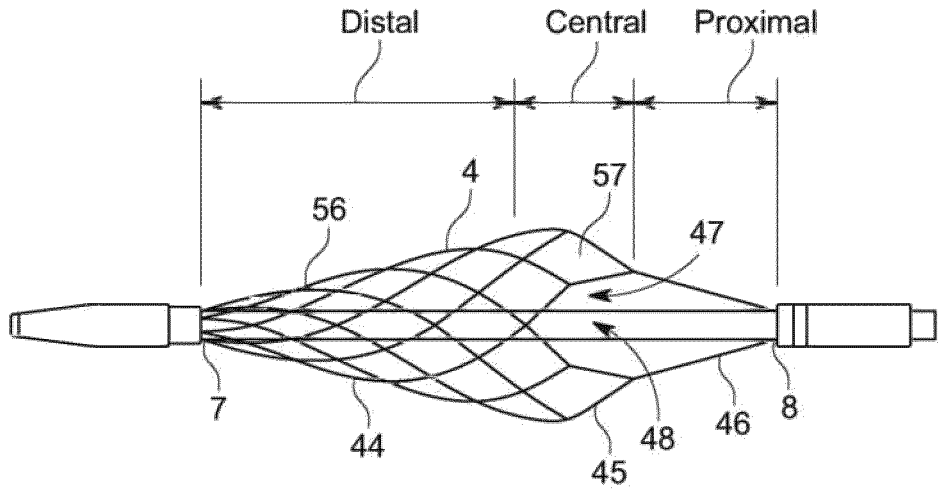
Figure 20:
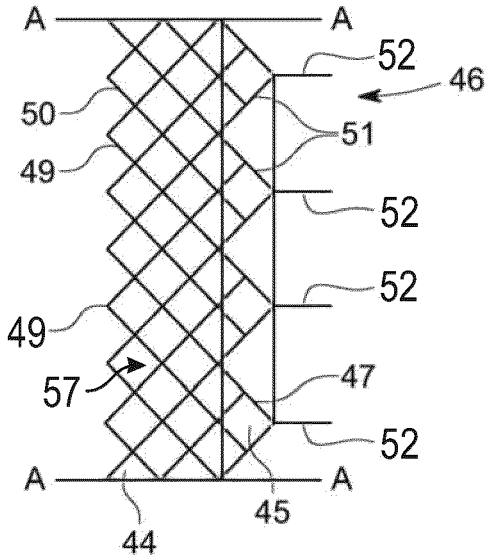

FIG. 8 is a side elevation of a further embodiment of the invention in which the device is provided with an over-ride mechanism to over-ride the biasing mechanism:

FIG. 9 is a side elevation of a further embodiment of the invention in which the device is provided with an extraction port for removing thrombus from the extraction mechanism;

FIG. 10 is an enlarged cross-sectional view of the extraction port and extraction mechanism:

FIG. 11 is a side elevation of a further embodiment of the invention in which catheter elements of the device can rotate and the device is provided with an outer sheath to prevent blood vessel trauma during device delivery:

FIG. 12 is a side elevation of a helical coil of an extraction mechanism in which the helical coil has a variable pitch notably a shorter pitch at the window and a longer pitch towards the handle:

FIG. 13 is an enlarged cross-sectional side view of a helical coil having a small diameter coil portion in a small diameter lumen and a large diameter coil portion in a large diameter lumen;

FIG. 14 is an enlarged cross-sectional side view of an alternative helical coil in which the cross-sectional area of the wire of the coil is reduced proximal to the proximal end of the extraction mechanism window in the distal arm;

FIG. 15 is a perspective view from above and one side of a radially expansible member with the extraction window located within the radially expansible member:

FIG. 16 is a perspective view from above and one side of a radially expansible member with the extraction window located proximal of and outside the radially expansible member on the distal arm;

FIG. 17 is a perspective view from above and one side of a radially expansible member with the extraction window located within the radially expansible member and having a longitudinal and circumferential axis on the distal control arm i.e. the extraction window being disposed circumferentially about the distal control arm;

FIG. 18 is an enlarged perspective view from above and one side of the extraction window of FIG. 17;

FIG. 19 is an enlarged side elevation of a radially expansible member having distinct or distinguishable distal, central and proximal zones, and FIG. 20 is an enlarged plan view of the braid or cut pattern of a portion of the radially expansible member of FIG. 19 at the distal, central and proximal zones.

DETAILED DESCRIPTION OF THE INVENTION

Synchronised Axial Movement of Extraction Mechanism and Control Arm

Figure 1:
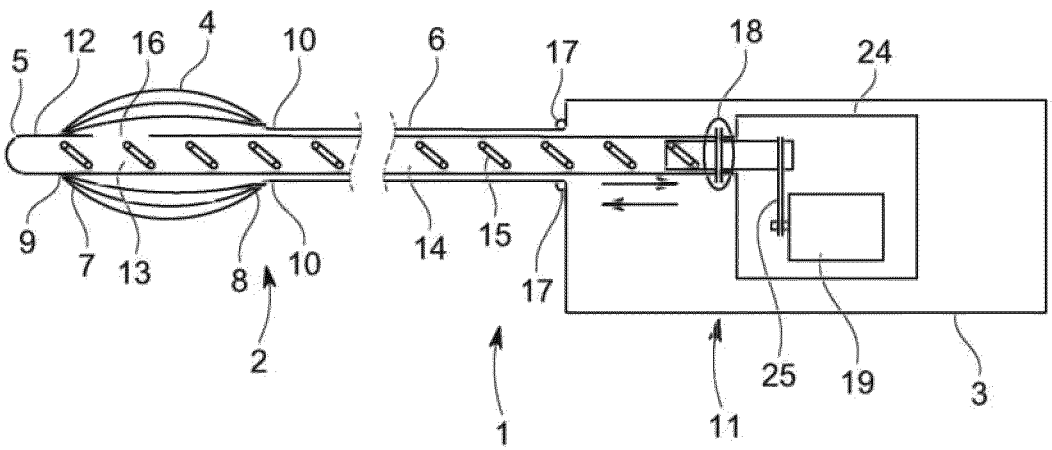
FIG. 1 is a side elevation of a first embodiment of a thrombectomy device of the invention in which axial movement of the extraction mechanism and the distal control arm containing the extraction mechanism is synchronised.
Figure 2:
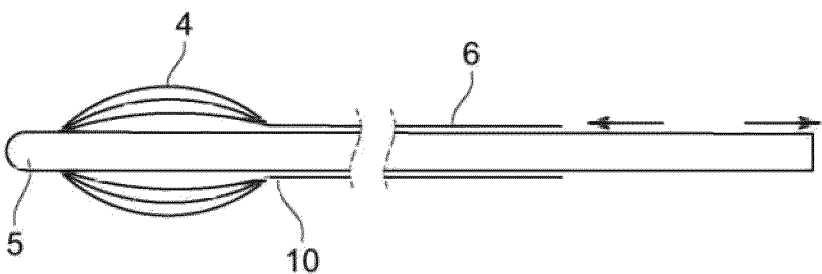
FIG. 2 is a side elevation of the radially expansible member and control arms of the device of FIG. 1 with the relative movement of the distal control arm indicated by the arrows.
Figure 3:
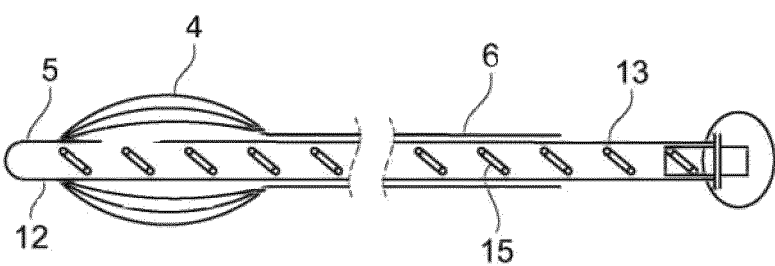
FIG. 3 is a side elevation of the lumen within the distal control arm housing the coil of the extraction mechanism with the distal control arm axially attached to the coil.

FIGS. 1 to 3 show a first embodiment of a thrombectomy device 1 of the invention made up of a controllable catheter member 2 having a handle 3 at a proximal end thereof and a compliant basket- or cage-like radially expansible member 4 for receiving thrombus at a distal end thereof. The controllable catheter member 2 is made up of an annular distal control arm 5 and an annular proximal control arm 6 partially surrounding and overlapping the distal control arm 5 with the radially expansible member 4 being attached to the distal control arm 5 at a distal end 7 of the radially expansible member 4 and to the proximal control arm 6 at a proximal end 8 of the radially expansible member 4. More particularly, the radially expansible member 4 is attached to the distal control arm 5 at its distal end 7 and to the proximal arm 6 at its proximal end 7 at respective operative connections 9,10 and the proximal control arm 6 is fixedly attached to the handle 3 at fixed connections 17 so that relative axial movement of the distal and proximal control arms 5,6 effects expansion and contraction of the radially expansible member 4 i.e. the proximal control arm 6 is operatively connected to the radially expansible member 4 and the distal control arm 5 is operatively connected to the radially expansible member 4 distally of the proximal control arm 6 connection.

Relative movement of the distal and proximal control arms 5,6, and in particular axial movement of the distal control arm 5 is effected by an operating mechanism 11 contained within the handle 3 so that the diameter/radial strength of the radially expansible member 4 can be adjusted in use.

The distal control arm 5 has an elongate tubular outer wall 12 extending from inside the handle 3 to the radially expansible member 4. Within the handle 3, the tubular outer wall 12 is attached to a distal control arm housing 24 contained within the handle 3.

The annular distal control arm 5, and more particularly the tubular outer wall 12, defines an elongate extraction lumen 13 extending between the housing 24 and the distal end of the distal control arm 5 for containing a thrombus extraction mechanism 14 which in the present embodiment includes a helical coil 15. As shown particularly in FIG. 12 described in more detail below, the helical coil 15 can have a variable pitch in which a short pitch 58 transitions to a longer pitch 59 at a transition zone 39 between the short and long pitches. The extraction mechanism 14 further includes a coil rotation mechanism 19 contained within the handle 3 and, more particularly, within the housing 24 attached to the distal control arm 5 in the handle 3. The helical coil 15 of the extraction mechanism 14 is actuated, i.e. rotated, by the coil rotation mechanism 19.

As the distal control arm 5 and the extraction mechanism 14 are combined in a single structure, the thrombectomy device 1 profile is reduced/minimised. This minimised or reduced profile allows the device 1 to gain access to areas within a confined anatomy.

The tubular outer wall 12 of the distal control arm 5 is provided with at least one elongate extraction window 16 through which the extraction mechanism 14 can make contact with a thrombus.

Accordingly, collected material can enter the extraction lumen 13 from inside or proximal to the radially expansible member 4. As will be appreciated by those skilled in the art, the tubular outer wall 12 can have more than one extraction window 16. In addition, the extraction window 16 can be an axial extraction window 16 on the tubular outer wall 16 or an end extraction window 16 located at the distal end of the distal control arm 5. In the present embodiment, the extraction window 16 is located on the tubular control arm 5 within the radially expansible member 4 and the helical coil 15 is axially adjacent to the extraction window 16 in the extraction lumen 13 so that material that enters the extraction window 16 into the extraction lumen 13 is positively displaced and transported along the extraction lumen 13 ensuring the extraction mechanism 14 does not get blocked.

Importantly, the thrombectomy device 1 is configured so that the extraction mechanism 14 and the distal control arm 5 are coupled to enjoy a synchronised axial movement. More particularly, the extraction mechanism 14 and the distal control arm 5 are configured to be coupled at the handle 3 to effect the synchronised axial movement. Accordingly, in the present embodiment, the helical coil 15 is connected to the tubular wall 12 of the distal control arm 5 at an axial connection 18 within the handle 3 so that the helical coil 15 is positionally axially fixed with respect to the distal control arm 5/extraction lumen 13 whilst being rotatable within the extraction lumen 13. More particularly, the helical coil 15 is axially fixed (i.e. axially and rotationally positionally fixed) with an axial connection 18 at only one end (in the present embodiment adjacent the housing 24) so that there is no tension on the helical coil 15 allowing easier rotation during operation and bending/flexing of the thrombectomy device 1. In general, the internal helical coil 15 is axially fixed with respect to the extraction lumen 13 at a minimum of one point.

As indicated above, the thrombectomy device 1 is provided with the coil rotation mechanism 19 within the housing 24 in the handle 3 to effect rotation of the helical coil 15. In the present embodiment, the coil rotation mechanism 19 is configured to translate axially within the housing 24 in synchronicity with the distal control arm 5—the rotation mechanism 19 within the housing 24 being axially fixed to the distal control arm 5 containing the extraction mechanism 14 whilst being axially moveable with respect to the handle 3. Accordingly, a drive train 25 between the rotation mechanism 19 and the helical coil 15 does not have to provide for axial movement of the helical coil 15 relative to the rotation mechanism 19 to maintain synchronicity.

Accordingly, axial movement of the extraction mechanism 14 i.e. the helical coil 15, the rotation mechanism 19 and the distal control arm 5 is synchronised during movement of the radially expansible member 4 between the contracted position and expanded positions to ensure that relative positioning of the transition zone 39 of the helical coil 15 to the extraction window 16 is maintained in use so that the extraction mechanism 14 operates effectively.

In a further embodiment of the invention, the extraction mechanism 14 can include an aspiration mechanism to further assist in transporting thrombus material through the extraction lumen 13 and to prevent blockage of the extraction lumen 13.

Figure 4:
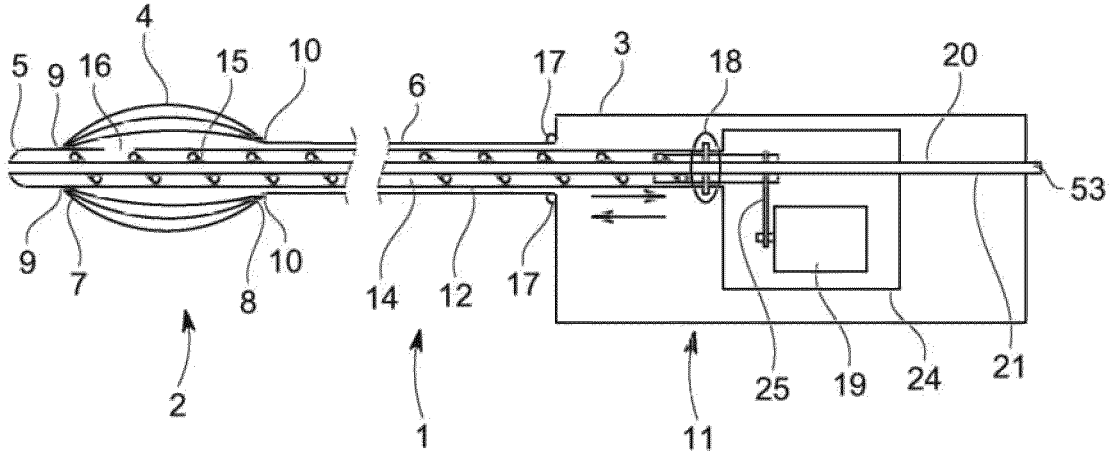
FIG. 4 is side elevation of a second embodiment of a thrombectomy device of the invention in which the distal control arm is also provided with a guidewire lumen for receiving a guidewire.
Figure 5:
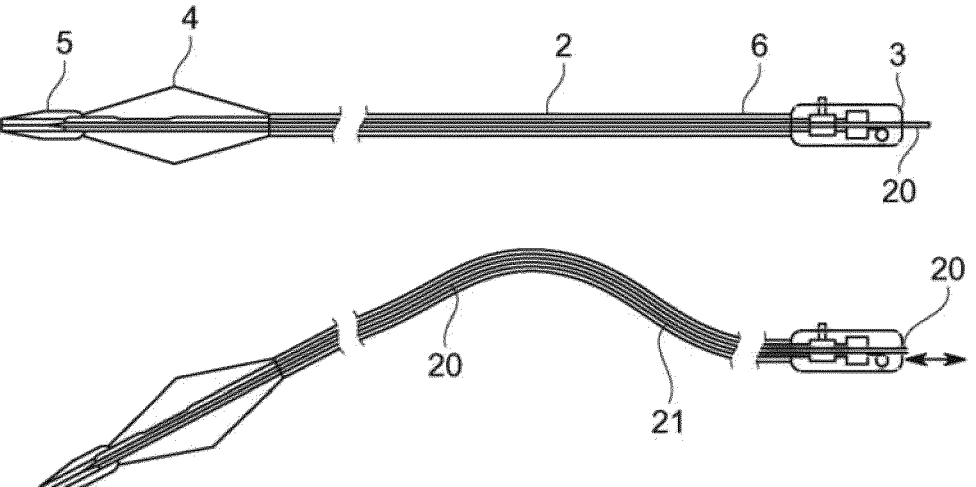
FIG. 5 shows side elevations of the thrombectomy device of FIG. 4 in which the guidewire lumen is axially moveable relative to the distal control arm with the axial movement indicated by arrows.

Synchronised Axial Movement of Extraction Mechanism and Control Arm with Guidewire Lumen FIGS. 4 and 5 show a second embodiment of a thrombectomy device 1 of the invention broadly similar to thrombectomy device 1 of FIGS. 1 to 3 but in which the thrombectomy device 1 is provided with an axially moveable guidewire lumen 20 for receiving a guidewire in use. Like numerals indicate like parts.

As shown in the drawings, the elongate guidewire lumen 20 extends centrally through the distal control arm 5 and is defined by an elongate tubular guidewire lumen wall 21 formed in the distal control arm 5 with the helical coil 15 of the extraction mechanism 14 positioned over the guidewire lumen wall 21. At its proximal end, the guidewire lumen 20 extends from the housing 24 within the handle 3 and exits the handle 3 at a guidewire lumen opening 53 to receive a guidewire in use.

The guidewire lumen 20, and more particularly the guidewire lumen wall 21, is fixedly connected at only one end thereof e.g. at the distal end of the radially expansible member or at the proximal end of the handle 3 so that compression of the guidewire lumen 20 and the helical coil 15 is prevented during bending of the thrombectomy device 1 (e.g. where the guidewire lumen wall 21 is fixed at both ends). Accordingly, in the present embodiment, the guidewire lumen wall 21 is fixed to the distal end 7 of the radially expansible member 4 and the helical coil 15 is axially fixed with respect to the extractor lumen 13 as previously described.

The use of a guidewire with the thrombectomy device 1 of the invention ensures the device can gain access to tortuous anatomy as it can be advanced over the guidewire.

Accordingly, in the present embodiment, the guidewire lumen 20 is axially moveable relative to the distal control arm 5 in the direction indicated by the arrows, at least on one end, so that axial freedom of movement to the guide wire lumen 20 is provided also allowing the device 1 to navigate through tortuous anatomy.

Figure 6:
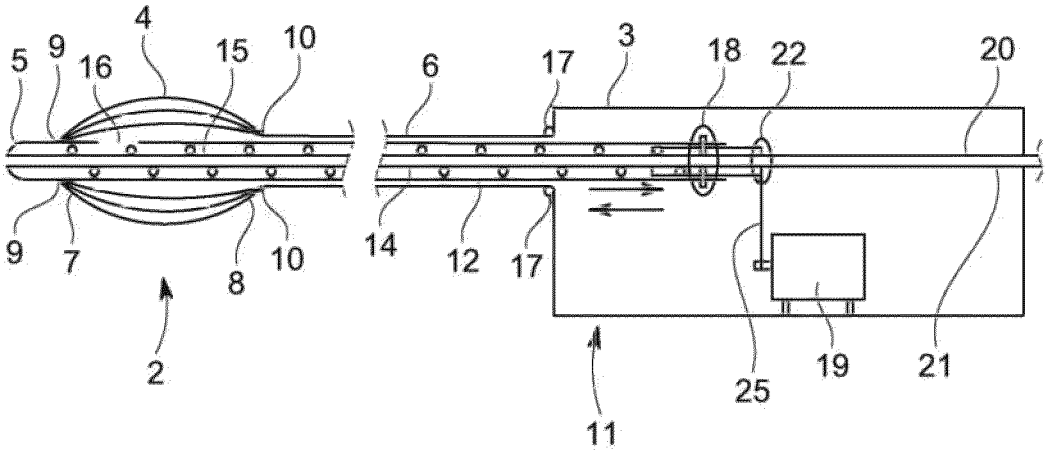
FIG. 6 is a side elevation of a further embodiment of the invention in which the rotation mechanism for rotating the helical coil of the extraction mechanism is fixedly attached to the handle of the device and the rotation mechanism is operatively connected to the helical coil.

The guide wire lumen 20 cannot rotate relative to the distal control arm 5 while the helical coil 15 rotates over the guide wire lumen 20 and the extraction lumen 13 remains stationary as described in FIGS. 1 to 3—i.e. the guidewire lumen 20 is not rotationally coupled to the helical coil 15. Accordingly, the extraction mechanism 14, i.e. the helical coil 15, achieves more effective friction between the guidewire lumen wall 21 of the guide wire lumen 20 and the material being transported to aid in ensuring the material does not rotate with the helical coil 15 and instead is transported axially. In addition, the non-rotating guide wire lumen 20 prevents the guide wire (inside it) from rotating.
Synchronised Movement of Coil Rotation Mechanism FIG. 6 shows a thrombectomy device 1 of the invention similar to the devices previously described having a variant of the synchronised coil rotation mechanism 19 in which the rotation mechanism 19 is fixedly attached to the handle 3 of the device 1. Like numerals indicate like parts.

As shown in the drawing, the housing 24 is omitted from the distal control arm 5 and the coil rotation mechanism 19 is fixedly attached to an internal face of the handle 24. Accordingly, in the present embodiment, the coil rotation mechanism 19, and in particular the drive train 25 of the coil rotation mechanism 19 is slidably operatively connected to the helical coil 15, via an operative connection 22 between the rotation mechanism 19 and the helical coil 15 to facilitate axial translation of the helical coil 15 while maintaining a rotational connection.

Figure 7:
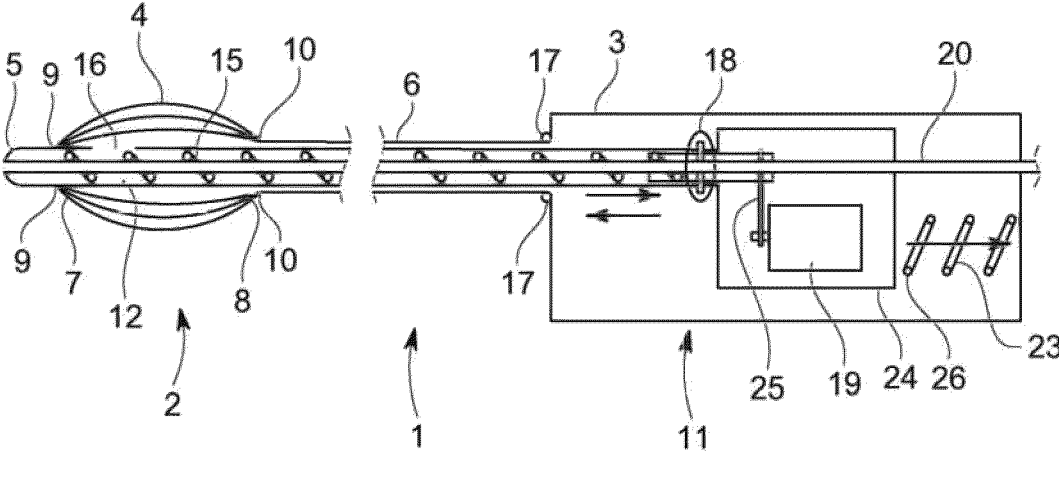
FIG. 7 is a side elevation of a further embodiment of the invention in which the extraction mechanism and the distal control arm are coupled via a biasing mechanism to bias the distal arm proximally relative to the handle/proximal arm to effect the synchronised axial movement of the extraction mechanism and the distal control arm.

Accordingly, the rotation mechanism 19 is fixedly connected to the handle 3/proximal arm 6 and is operatively connected to the coil 15 thus allowing axial movement of the extraction mechanism 14 relative to the rotation mechanism 19. As a result, the drive train 25 between the rotation mechanism 19 and the helical coil 15 facilitates axial translation of the helical coil 15 relative to the rotation mechanism 19 reducing the space requirement within the handle 3 and reducing the mass of the extraction mechanism 14 that translates axially.
Biasing Mechanism Coupling FIG. 7 shows a further embodiment of the invention, similar to the embodiments previously described in which the thrombectomy device 1 is configured so that the extraction mechanism 14 in the form of the helical coil 15 and the distal control arm 5 are coupled at the handle 3 to effect the synchronised axial movement and like numerals indicate like parts. However, in the present embodiment, the extraction mechanism 14 and the distal control arm 5 are configured to be coupled at a biasing mechanism 23 in the handle 3 to bias the distal arm 5 relative to the handle 3/proximal arm 6.

Similarly, in the embodiment described in FIG. 6, the biasing mechanism 23 could be coupled directly or indirectly to the distal arm 5 relative to provide the bias with respect to the handle 3/proximal arm 6.

Like numerals indicate like parts. As shown in the drawing, in the present embodiment, the biasing mechanism 23 is disposed between the housing 24 of the distal arm 5 and the handle 3 to bias the extraction mechanism 14 of the distal arm 5 proximally or distally relative to the handle 3/proximal arm 6. Accordingly, an axial biasing force is provided to the radially expansible member 4 biasing it into an expanded position as required.

In one embodiment, the biasing mechanism 23 delivers a substantially constant force to assist in controlling the outward radial force of the radially expansible member 4.

As shown in the drawing, the biasing mechanism 23 can be a spring 26 such as a constant force spring 26.

As previously described, synchronized axial movement of the helical coil 15 and the distal control arm 5 during movement of the radially expansible member 4 between the contracted position and expanded positions ensures the relative positioning of the transition zone 39 of the helical coil 15 to the extraction window 16 is maintained thus ensuring the extraction mechanism 14 operates effectively.

FIG. 8 shows a side elevation of a further embodiment of the invention similar to the devices previously described but in which the device 1 is provided with a manually operable over-ride mechanism 36 to over-ride the biasing mechanism 23. The over-ride mechanism 36 extends from the handle housing 54 and is manually operable by a user.

The over-ride mechanism 36 is configured to exert an axial force on the distal control arm 5 which contains the extraction mechanism 14 in an opposite direction to the force applied to the distal control arm 5 by the biasing mechanism 23 to allow a user to collapse the radially expansible member 4 when required. In the present embodiment, the over-ride mechanism 36 extends outwards from the distal control arm housing 24 contained within the handle 3 and through the handle housing 54 for manual activation by a user. The over-ride mechanism 36 can be in the form of a cam, a linear actuator, an electrically driven device or the like.

In a further embodiment of the invention, the biasing mechanism 23 can include defined axial travel limiting stops 60 to limit travel and prevent axial over-travel of the distal control arm 5 to ensure that the radially expansible member 4 is not stretched beyond its operating range. As shown in the drawing, in the present embodiment, the travel limiting stops 60 are disposed either side of and spaced apart from the biased distal control arm housing 24 to limit travel of the distal control arm housing 24 and hence the extraction mechanism 14. The travel limiting stops 60 can be in the form of spaced apart fingers 60 extending inwards from the handle housing 54.

Furthermore, as shown in the FIG. 8, in a further embodiment of the invention, the radially expansible member 4 can be provided with one or more radially expansible member or basket blockers 61 to prevent radially expansible member inversion in use. In the present embodiment, the blockers 61 are a pair of oppositely disposed spaced blockers 61 disposed adjacent the operative connections 9,10. The blockers 61 can be mounted on the tubular wall 12 of the distal control arm 5.
Extraction Port FIGS. 9 and 10 show a side elevation of a further embodiment of the invention similar to the embodiments previously described in which the device 1 is provided with a tubular extraction port 27 extending laterally outwards from the handle 3 for extracting thrombus from the extraction mechanism 14. Like numerals indicate like parts.

As shown in the drawings, generally, the laterally extending extraction port 27 extends outwards from the tubular wall 12 of the distal control arm 5, and optionally the handle 3, adjacent to or proximal of the proximal end of the helical coil 15 at the handle 3 so that the extraction port 27 is in fluid communication with the extraction lumen 13. The extraction port 27 can be integral with the extraction mechanism 14 or, as shown in the drawing, can be configured to be part of an extraction port insert 28 inserted in and contiguous with the distal arm 5 and the extraction mechanism 14. In this format, the insert 28 has a cylindrical wall 29 sized and shaped to engage with the distal control arm 5 defining a helical coil 15 receiving bore 30 contiguous with the extraction lumen 13 to receive material from the helical coil 15. The insert 28 is further provided with an elongate cylindrical member 31 inserted in the helical coil 15 and a terminal seal 32 to prevent leakage from the insert 28.

The extraction port 27 facilitates material (thrombus) to be removed from the extraction mechanism 14 to a location outside the handle 3 through a handle opening 33 in the handle housing 54 without leakage of thrombus inside the device 1 while still facilitating rotation of the helical coil 15. The central longitudinal axis of the outwardly extending extraction port 27 is oriented at an angle of 0-90 degrees to the central axis of the helical coil 15 to optimise the efficacy of thrombus exiting from the extraction mechanism 14.

As shown in the drawings, the proximal end of the helical coil 15 is attached to the cylindrical member 31 and the cylindrical member 31 is at least partially contained within the extraction port 27 so that it is possible to seal around the cylindrical member 31 which, being attached to the helical coil 15, can form part of the coil rotating mechanism 19 to rotate the helical coil 15.

The seal 32 is located adjacent to the extraction port 27 and the cylindrical member 31 as this is the location where leakage is likely to occur.

In one embodiment, the cylindrical member 31 has a cylindrical member lumen for receiving a guide wire lumen 20 and is rotatable about the guide wire lumen 20 to enable the use of a guide wire with the device 1. In another embodiment, an additional sealing member can form a seal between the rotatable cylindrical member lumen and the guide wire lumen 20 to prevent leakage.

Rotatable Catheter Elements Sheath

FIG. 11 shows a side elevation of a further embodiment of the invention similar to the device shown in FIG. 9 in which catheter elements such as the extraction mechanism 14 of the device in the handle 3 can be translated axially as previously described. Like numerals indicate like parts. However, in the present embodiment, the device 1 is provided with an outer sheath to prevent blood vessel trauma and, optionally, some catheter elements of the device 1 can be configured to rotate.

More particularly, as shown in the drawing, the device 1 is also provided with an outer sheath 35 to prevent blood vessel trauma in use. The outer sheath 35 extends over the exposed portion of the proximal control arm 6 to prevent the device 1 from causing vessel trauma when navigating to a treatment zone. Additionally, the outer sheath 35 can be axially slidably moveable as indicated by the arrows to expose and cover the expansible member 4 in use as required.

As shown in the drawing, in this embodiment, the handle housing 54 can be provided with guides 34 adjacent the proximal arm 6 to facilitate the axial movement of the sheath 35.

Optionally, in a further embodiment which may or may not include a sheath 35 as outlined above, some device elements can be configured to be rotatable if desired. In one embodiment, the device 1 is configured to facilitate rotation of the expansible member 4 and the distal/proximal control arms 5,6 to aid in separating thrombus from vessel walls.

Additional guides 34 can facilitate the rotation movement thereby providing a mechanism for components to slide and rotate as required.

As will be appreciated by those skilled in the art, if required, the guides 34 in the handle housing 54 can be configured to facilitate axial only movement of the extraction mechanism 14 within the distal control arm 5. Accordingly, the extraction mechanism 14/distal control arm 5 can translate axially to expand and collapse the radially expansible member 4 whilst ensuring there is no rotation of the distal control arm 5 relative to the proximal control arm 6 and thereby also ensuring there is no twist introduced to the radially expansible member 4 in use.

As described above, the extraction mechanism 14 can also be biased in a specific axial direction (either proximal or distal) by the biasing mechanism 23 to provide an axial force to the radially expansible member 4 e.g. biasing it into an expanded position.

Helical Coil

FIGS. 12 to 14 show helical coil 15 configurations suitable for use in thrombectomy devices 1.

As shown in FIG. 12, the helical coil 15 of the extraction mechanism 14 can have a variable pitch e.g. a relatively shorter pitch (the short pitch) 58 towards or at the distal end, i.e. at or adjacent the extraction window 16 and a relatively longer pitch (the long pitch) 59 proximally of the short pitch 58.

The variable pitch provides relief/space/freedom to the materials being extracted, allowing it to be transported easier through the extraction lumen. More particularly, a short pitch 58 at the extraction window 16 ensures that an increased number of extraction "bites" are taken from thrombus material per rotation by the helical coil 15 relative to the extraction window 16, to efficiently collect thrombus and convey the thrombus into the extraction mechanism 14 within the distal control arm 5 whilst also allowing more time for a thrombus to enter the extraction lumen 13. The received material is then conveyed by the helical coil 15 to the longer or increased pitch 59 of the helical coil 15 so that it is no longer tightly packed between the loops of the helical coil 15. Blockages of the extraction mechanism 14 are therefore prevented. In addition, the longer pitch 59 increases the extraction rate (i.e. axial movement of material) of the extraction mechanism 14.

In one embodiment, the distal portion of the helical coil 15 has a pitch proportional to the rotational speed and the diameter of the helical coil to allow for more effective/efficient transport of the material.

In another embodiment, the proximal portion of the helical coil (the longer pitch 59) has a pitch of 1-5 times the distal pitch (the shorter pitch 58). The Applicant has found that this pitch relationship between the shorter and longer pitch helps to ensure that the extraction mechanism 14 does not block in use.

As indicated above, typically the extraction window 16 is located axially adjacent to the shorter pitch 58 at the distal end to ensure that material entering the extraction lumen 13 is easier to transport. In one embodiment, the shorter pitch 58 starts to transition to a longer pitch 59 close to the proximal end of the extraction window 16 to minimise the distance the material travels while in the short pitch 58 and hence also reduce the potential for the extraction mechanism to get blocked.

The shorter pitch 58 can therefore transition to the longer pitch 59 at a pitch transition zone 39 which preferably starts within a distance defined by approximately 10 times the pitch distal to the proximal end of the extraction window 16 which also minimises the distance the material travels at the short pitch 58 and hence reduces the potential for the extraction mechanism 14 to block in use. This also speeds up the overall extraction time of a captured thrombus. The length of the transition zone 39 is preferably less than a distance defined by 10 times the distal pitch, and is positioned proximal of the proximal end of the extraction window 16 which serves to minimise the distance extracted material travels at the shorter pitch at the extraction window 16 and hence further reduces the potential for the mechanism to get blocked during use.

FIG. 13 shows an enlarged cross-sectional side view of a helical coil 15 of an extraction mechanism 14 in which the helical coil 15 is made up of a (distal) small diameter coil portion 40 at or adjacent the extraction window 16 and a (proximal) large diameter coil portion 41 contiguous with the small diameter coil portion 40 disposed towards the handle 3. More particularly, as shown in the drawing, the extraction lumen 13 is made up of a distal relatively smaller diameter extractor lumen portion 37 (the small diameter lumen) at the extraction window 16 and a proximal relatively larger diameter lumen portion 38 (the large diameter lumen) i.e. the inner diameter of the extraction lumen 13 increases proximal to the extraction window 16. In the present embodiment, the transition zone 39 is defined between the small and large diameter lumens 37,38. Optionally, the small diameter coil may be the same as the large diameter coil within the small and large diameter lumen.

The large diameter lumen 38 provides relief/space/freedom to extracted material allowing it to be transported easier through the extraction lumen 13.

As indicated above, the diameter of the diameter of the helical coil 15 preferably increases at the large diameter coil portion 41 adjacent to the large diameter lumen 38. This prevents extracted material from flowing uncontrollably between the outer diameter or edge of the helical coil 15 and the internal diameter or edge of the extraction lumen 13.

FIG. 14 shows an enlarged cross-sectional side view of an alternative helical coil 15 in which the elongate wire of the helical coil 15 has a variable thickness or cross-sectional area. More particularly, the elongate wire of the helical coil 15 has a relatively larger cross-sectional area portion 42 (the large cross-sectional area portion) and a relatively smaller cross-sectional area portion 43 (the small cross-sectional area portion). The small cross-sectional area portion 43 is disposed towards the proximal end of the extraction lumen while large cross-sectional area portion is disposed towards the distal end at the extraction window 16 i.e. the cross-sectional area of the helical coil wire reduces proximal to the proximal end of the extraction tube window 16 to provide space/relief to the material being transported through the extraction lumen 13 preventing it from getting blocked.

Extraction Window

FIGS. 15 to 18 show various optional configurations of the extraction window 16 on the distal control arm 5. Like numerals indicate like parts. Generally, the extraction window can be positioned within and/or proximal and/or distal to the radially expansible member 4 and is made up of an elongate axial window 16 defined in the tubular wall 12 of the distal control arm 5 to provide access to the helical coil 15 of the extraction mechanism 14 in the extraction lumen 13.

In the embodiment shown in FIG. 15, the extraction window 16 located or positioned within the radially expansible member 4 on the distal control arm 5. The extraction window 16 is located towards the distal end 7 of the radially expansible member 4 Accordingly, the extraction window

16 effectively removes material from inside the radially expansible member 4 which can gather at the distal end 7 of the radially expansible member 4. Accordingly, in use, such an extraction window 16 can remove thrombus material within and proximal of the radially expansible member 4 and also remove any material that may be pushed proximal of the radially expansible member 4.

FIG. 16 shows an alternative arrangement in which the extraction window 16 is located proximal to and outside the radially expansible member 4 on the distal arm 5 i.e. proximal of the proximal end 8 of the radially expansible member 4. This serves to remove material proximal of the radially expansible member 4 which in use may be pushed proximal of the radially expansible member 4 and must therefore be extracted.

In one embodiment of the invention, the thrombectomy device 1 can further include a macerator or cutting mechanism to macerate extracted material and the extraction window 16 and the helical coil 15 can in combination co-operate to form the macerator/cutting mechanism. Accordingly, material being extracted can be macerated via a shearing action provided by the interaction between the helical coil 15 and the extraction window 16. In all embodiments described, the helical coil may comprise of coiled wire(s) or cut tube profiles with different cross sectional profiles, including round, ovoid, square, rectangular, triangular or other profiles suitable for cutting and extraction when rotated.

FIGS. 17 and 18 show a radially expansible member 4 with the elongate extraction window 16 located within the radially expansible member as shown in FIG. 15. However, in the present embodiment, the elongate extraction window 16 is shaped and configured to have both a longitudinal and circumferential axis along the distal control arm 5 i.e. the extraction window 16 is disposed circumferentially about the distal control arm 5. The circumferential axis increases/decreases the shearing action between the helical coil 15 and the extraction window 16 to effectively generate a scissor-like cutting action between the helical coil 15 and the extraction window 16 to provide an optimal macerating action on the material being extracted.

Radially Expansible Member Geometry

FIGS. 19 and 20 show a radially expansible member 4 suitable for use with a thrombectomy device 1.

As shown in the drawings, the radially expansible member 4 is in the form of a braided cage 4 having distinct or distinguishable distal, central flexible and proximal zones 44, 45, 46 respectively formed for example from braided or twisted material such as wires 56 which in turn define apertures 57 in the radially expansible member 4. As previously described, the radially expansible member 4 has a distal end 7 in the distal zone 44 and a proximal end 8 defining a thrombus receiving opening 48 in the proximal zone 46. The radially expansible member may also be formed from a cut or formed profile to form the desired distal, central flexible and proximal zones 44, 45, 46 respectively.

The distinct zones 44, 45, 46 within the radially expansible member 4 can be individually tailored to give different mechanical properties as required.

In one embodiment, the distal zone 44 has a reduced porosity relative to the proximal zone 46 i.e. the apertures 57 at the proximal end 8 are large to accept thrombus into the radially expansible member 4 and the apertures 57 at the distal end 7 are small to prevent thrombus from leaving the radially expansible member 4. The distal end 7 may also be coated or attached to a permeable or impermeable membrane to further reduce or eliminate the porosity of the distal end 7.

The central zone 45 has a circumferential edge 47 defining the thrombus receiving opening 48. The circumferential edge 47 has a serrated configuration and acts as a cutting wire to separate thrombus from vessel walls. In alternative embodiments, the circumferential edge 47 can have a sharp or angled edge having other outline shapes as required.

In another embodiment, the central zone 45 is more radially compliant than the distal and proximal zones 44, 46 respectively. Accordingly, when the radially expansible member 4 is expanded, the central zone 45 expands first so that the circumferential edge 47 is at (or close to) the largest diameter possible for the radially expansible member 4.

FIG. 20 shows a plan view of a suitable braid pattern 49 of a portion of the radially expansible member 4 at the distal, central and proximal zones 44, 45, 46 respectively. As shown in the drawing, the braid pattern 49 is made up braided single wires 50 defining the apertures 57 in the distal zone 44, twisted double wires (i.e. two twisted wires) 51 forming single braid wires 51 in the transition zone 45 and four twisted wires 52 forming single braid wires 51 in the proximal zone 46. In other embodiments, the pattern 49 may be made from a cut or formed profile, where the proximal members may optionally be comprised of a larger cross sectional profile or of a different material to provide additional strength or resistance to bending during use.

In the embodiment shown in FIGS. 19 and 20, the radially expansible member 4 is made up of varying arrangements of twisted braided wires to form the proximal, central and distal zones 44, 45, 46. Varying the wires as described above varies the properties of the radially expansible member 4 in the distal, central and proximal zones 44, 45, 46 so that the apertures 57 at the proximal end 8 are large to accept the thrombus into the radially expansible member 4 and the apertures 57 at the distal end 7 are small to prevent the thrombus from leaving the radially expansible member 4. Moreover, the transition from single wires 50 to twisted wires 51, 52 creates a central zone 45 in the structure at the circumferential edge 47 that is the first to expand in use and ensures the circumferential edge 47 is at or close to the largest outer diameter of the radially expansible member 4.

The invention claimed is:

1. A thrombectomy device for removing matter from a body lumen comprising:
   a handle including a distal control arm housing;
   a catheter member extending from the handle, the catheter member having a distal control arm and a proximal control arm;
      wherein the proximal control arm at least partially surrounds the distal control arm;
   a radially expansible member coupled to the distal control arm proximate to a distal end of the radially expansible member, and the radially expansible member coupled to the proximal control arm along a proximal end of the radially expansible member;
      wherein the radially expansible member is configured to transition between a contracted position and an expanded, thrombus-capture, position in response to axial movement of the distal control arm relative to the proximal control arm;
   a thrombus extraction mechanism, including a helical coil, extending through the distal control arm; and
   a rotation mechanism attached to the distal control arm and the rotation mechanism is in or adjacent to the distal control arm housing;

wherein the rotation mechanism includes a drive train slidably connected to the thrombus extraction mechanism, the drive train configured to facilitate axial translation of the helical coil of the thrombus extraction mechanism;
   wherein the thrombus extraction mechanism and the distal control arm are configured to be coupled to effect axial movement so that the thrombus extraction mechanism is positionally axially fixed with respect to the distal control arm;
   wherein the rotation mechanism is configured to translate axially within or adjacent to the distal control arm housing.

2. The thrombectomy device as claimed in claim 1, wherein the thrombus extraction mechanism and the distal control arm are configured to be coupled at the handle to effect synchronized axial movement.

3. The thrombectomy device as claimed in claim 1 further comprising: at least one extraction window on the distal control arm; wherein the at least one extraction window is positionally axially fixed with respect to the helical coil and the at least one extraction window has a longitudinal and circumferential axis along the distal control arm.

4. The thrombectomy device as claimed in claim 3 wherein the helical coil comprises a shorter pitch at or adjacent the at least one extraction window and a longer pitch towards the handle.

5. The thrombectomy device as claimed in claim 1 wherein the helical coil includes a distal small diameter coil portion proximate to an extraction window on the distal control arm and a proximal large diameter coil portion contiguous with the small diameter coil portion towards the handle.

6. The thrombectomy device as claimed in claim 1 wherein the helical coil has a variable thickness or cross-sectional area.

7. The thrombectomy device as claimed in claim 1 wherein the thrombus extraction mechanism and the distal control arm are coupled at a biasing mechanism in the distal control arm housing.

8. The thrombectomy device as claimed in claim 7 wherein the biasing mechanism biases the thrombus extraction mechanism proximally or distally relative to the proximal control arm.

9. The thrombectomy device as claimed in claim 7 further comprising a manually operable over-ride mechanism to over-ride the biasing mechanism.

10. The thrombectomy device as claimed in claim 1 further comprising a guide wire lumen through the catheter member.

11. The thrombectomy device as claimed in claim 1 wherein the thrombus extraction mechanism is positioned over a guidewire lumen and the guidewire lumen is not rotationally coupled to the thrombus extraction mechanism.

12. The thrombectomy device as claimed in claim 1 further comprising an extraction port in fluid communication with the thrombus extraction mechanism for extracting thrombus from the thrombus extraction mechanism.

13. The thrombectomy device as in claim 1 wherein the thrombus extraction mechanism and the distal control arm are configured to translate axially in a synchronized movement; and
   wherein the rotation mechanism is configured to translate axially within the distal control arm housing with the distal control arm in a synchronized movement.

* * * * *